United States Patent [19]

Hillman et al.

[11] Patent Number: 5,135,719
[45] Date of Patent: Aug. 4, 1992

[54] BLOOD SEPARATION DEVICE COMPRISING A FILTER AND A CAPILLARY FLOW PATHWAY EXITING THE FILTER

[75] Inventors: Robert S. Hillman, Cupertino; Ian Gibbons, Menlo Park, both of Calif.

[73] Assignee: Biotrack, Inc., Mountain View, Calif.

[21] Appl. No.: 607,618

[22] Filed: Oct. 23, 1990

Related U.S. Application Data

[60] Continuation of Ser. No. 163,392, Mar. 2, 1988, abandoned, which is a division of Ser. No. 924,633, Oct. 29, 1986, Pat. No. 4,753,776.

[51] Int. Cl.$^5$ .................. G01N 1/18; G01N 21/01
[52] U.S. Cl. ................... 422/101; 422/58; 436/177; 436/824; 435/2; 435/240.2; 210/509; 210/503
[58] Field of Search ............... 422/58, 66, 101; 435/2, 435/240.2; 436/69, 177, 824; 210/503, 505, 508, 509

[56] References Cited

U.S. PATENT DOCUMENTS 3,843,324 10/1974 Edelman et al. ................ 435/2
4,327,073 4/1982 Huang ........................ 422/66
4,426,451 1/1984 Columbus ..................... 436/177
4,623,461 11/1986 Hossom et al. ................. 422/101
4,692,411 9/1987 Ghose ......................... 436/824
4,753,776 6/1988 Hillman et al. ................ 422/101
4,808,533 2/1989 Fabricius et al. .............. 435/240.2
4,816,224 3/1989 Vogel et al. .................. 422/101
4,843,017 6/1989 Oberhardt et al. .............. 422/101
4,933,092 1/1990 Aunet et al. .................. 210/729

Primary Examiner—Robert J. Hill, Jr.
Assistant Examiner—David Redding
Attorney, Agent, or Firm—Cooley Godward Castro Huddleson & Tatum

[57] ABSTRACT

A method for separating plasma from red blood cells and a device utilizing the method in which a low-pressure filter is interposed in a pathway between an inlet port and a reaction area. The sole driving force for the movement of plasma from the filter to the reaction area is capillary force provided by a tubular capillary. The filter is selected from glass microfiber filters of specified characteristics, which can operate in the absence of agglutinins, and filters capable of separating agglutinated red cells from plasma, which require the use of an agglutinin.

7 Claims, 2 Drawing Sheets

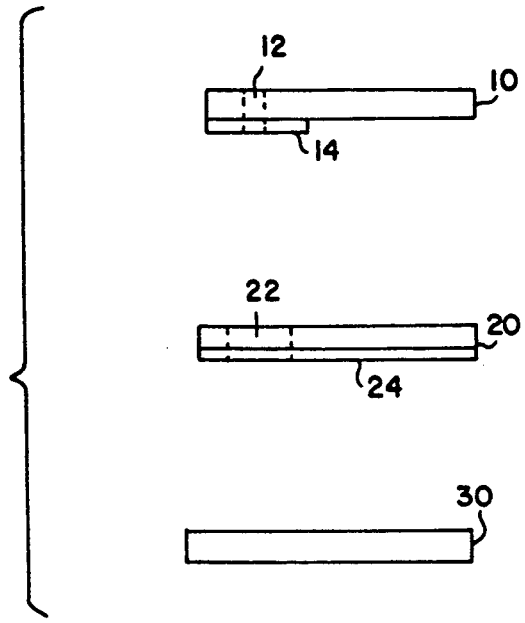
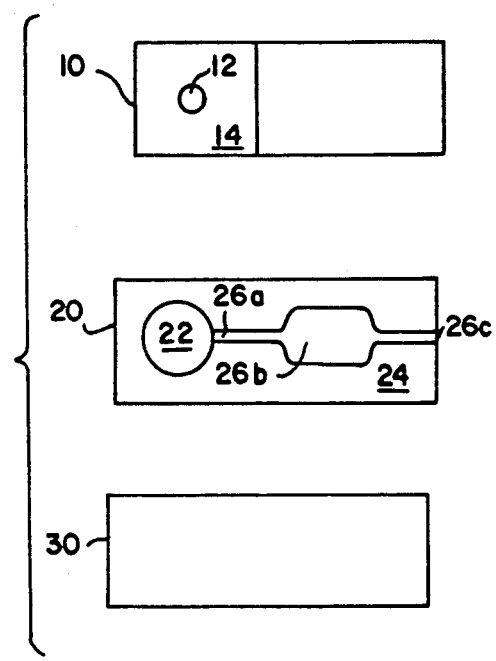
FIG. 1a   FIG. 1b
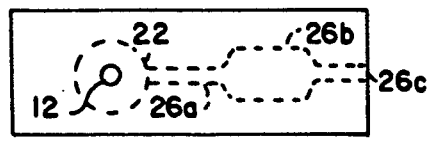
FIG. 1c

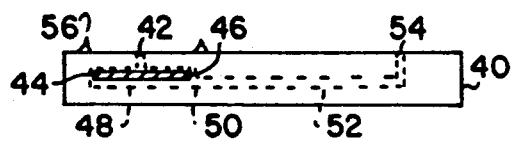
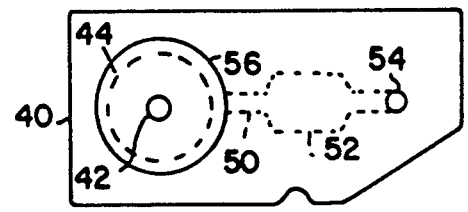
FIG. 2a  FIG. 2b
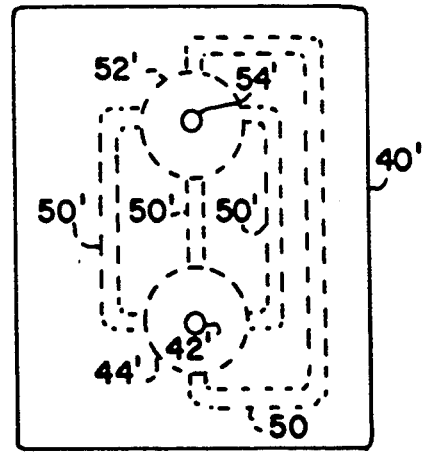
FIG. 3

BLOOD SEPARATION DEVICE COMPRISING A FILTER AND A CAPILLARY FLOW PATHWAY EXITING THE FILTER

This application is a continuation of U.S. application Ser. No. 07/163,392, filed Mar. 2, 1988, now abandoned, which is a division of U.S. application Ser. No. 924,633, filed Oct. 29, 1986, now U.S. Pat. No. 4,753,776.

BACKGROUND OF THE INVENTION

1. Field of the Invention

This invention relates to techniques and devices for separating plasma from blood by filtration and is particularly directed to filtration at low pressures.

2. Description of the Background

Many diagnostics are carried out in the clinical field utilizing blood as a sample. Although some of these techniques can be carried out on whole blood, it is necessary in many instances to utilize serum or plasma as the sample in order to obtain an accurate reading. For example, red blood cells (erythrocytes) scatter and absorb light and could adversely affect a measurement of either reflected or transmitted light of a diagnostic test relying on either of these measurement techniques.

Traditionally, plasma and serum have been separated from whole blood by centrifuging either before (for plasma) or after (for serum) clotting. However, centrifugation is time consuming and requires equipment that is not generally available outside the clinical laboratory. Accordingly, field testing of numerous blood substances that require serum or plasma is difficult.

A number of techniques have been devised to avoid this problem. The techniques generally utilize a filtering device capable of separating red blood cells from plasma. Numerous materials have been used in the past to form filters. Paper, non-woven fabric, sheet-like filter material composed of powders or fibers such as man-made fibers or glass fibers, and membrane filters having suitable pore sizes have been proposed. For example, U.S. Pat. No. 4,256,693 to Kondo et al. discloses a number of filter materials in a multi-layered integral chemical analysis element for use with blood. U.S. Pat. No. 4,477,575 to Vogel et al. describes a composition and process for permitting the separation of plasma or serum from whole blood utilizing glass fibers in combination with other absorbent layers.

However, these prior art techniques have proven to be unsuitable for use in applications which, because of space and volume restraints, can only utilize a small filter in a device in which a single drop of blood is separated and the plasma is transported through the device solely by means of capillary action. Accordingly, further refinement in blood separation techniques is desirable.

SUMMARY OF THE INVENTION

A device and a technique for separating red blood cells from plasma are provided in which a whole blood sample is applied to a filter under conditions in which the driving force for transporting the plasma from the exit face of the filter is provided solely by capillary action. Two basic filtering techniques can be used. The first utilizes a glass microfiber filter and does not require the use of red cell agglutinins (although an agglutinin can be used if desired). The second requires the use of agglutinins but can employ a wide variety of filters. The glass microfiber filter is selected in terms of particle size retention and thickness to allow plasma to pass more rapidly through the filter than the red blood cells, whose passage through the filter is retarded in a manner similar to that which occurs in chromatography columns. Although the red blood cells eventually pass through the filter, sufficient plasma has separated and passes by capillary action to a reaction chamber to allow analysis of the analyte present in the plasma without interference by the red blood cells. When agglutinins are used, the filter can be any filter capable of separating agglutinated red blood cells from plasma. However, both techniques are specially adapted for use with small volumes of blood and the low pressures available for use in transporting blood in capillary devices.

BRIEF DESCRIPTION OF THE DRAWINGS

FIGS. 1a, 1b, and 1c show one embodiment of a filter-containing device of the invention in which a number of examples described below were carried out in which FIG. 1a is an expanded side view, FIG. 1b is a bottom view of each of the components making up the final device, and FIG. 1c is a top view of the assembled device.

FIGS. 2a and 2b show an embodiment of a filter-containing device of of the invention in which two or more plastic forms are welded to form a unitary device having internal chambers in which FIG. 2a is a side view and FIG. 2b is a top view of the unitary device after welding.

FIG. 3 is a top view of a filter-containing device of the invention having multiple pathways for the passage of separated plasma to a reagent chamber.

DESCRIPTION OF PREFERRED EMBODIMENTS

The present invention may be carried out in the capillary flow device that is described in detail in U.S. application Ser. No. 880,793, filed Jul. 1, 1986, which is a continuation-in-part of U.S. application Ser. No. 762,748, filed Aug. 5, 1985 both of which are commonly assigned, co-pending applications. The capillary flow device described in these earlier applications relies upon capillaries, chambers, and orifices to pump fluids; to control measurement of fluids, reaction times, and mixing of reagents; and to determine a detectable signal. The capillaries provide the sole driving force for the movement of liquid through the device.

Although these devices could be utilized with whole blood as previously described, use with serum or plasma required separation of red blood cells prior to application of the serum or plasma to the device. The present invention allows application of whole blood directly to these devices or to any other devices which rely on capillary action to provide the driving force for the movement of fluids. By selecting glass fiber filters or combinations of agglutinins and either glass or non-glass filters as described in this specification, it is possible to accomplish the desired separation in a very small space with a minimum of cell lysis and without requiring the application of any additional force other than that which is supplied by capillary action to move the serum or plasma to a reaction chamber.

One useful aspect of the invention is that separation of red blood cells from plasma can be accomplished utilizing a single layer of filter material and a small volume of blood. Prior art materials used for blood separation on a larger scale and/or utilizing multiple-layer filters with absorbent layers have proven not to be useful under the present conditions for separation.

A key part of a first embodiment of the present device is a glass fiber filter. Particularly suitable glass fiber filters can be prepared from fibers of borosilicate glass, a material that contains, in addition to silicon dioxide, approximately 10% of boron trioxide as well as alkali and alkaline earth oxides and oxides of other metals such as iron, aluminum, and zinc. However, other glasses can also be utilized.

In the production of glass fiber filtering media of the invention, microglass fibers are utilized. These are extremely fine fibers typically formed by blowing glass through jets as opposed to spun glass material made from drawn glass filaments. Typically, glass fiber filters are prepared from fibers with diameters between 0.10 and 7.0 μm.

However, it is important to control the distribution of fibers present within this diameter range in order to prepare a glass fiber filter that will be useful in the practice of this invention. A narrow range of fine fibers with a minimum of large diameter fibers should be used.

A preferred filter will have 60%, preferably 80% or more, of its fibers with diameters from 0.10 to 1.23 μm and no more than 40%, perferably no more than 20%, with diameters larger than 1.23 μm. Filters with essentially all of their fibers having diameters less than 4.00 μm are preferred.

On the other hand, the range of fiber sizes should not be too small within the limits outlined above. A relatively even distribution of diameters in the range of 0.10 to 1.23 μm is preferred. An extremely narrow range of fiber diameters (varying over a total range of 0.14 μm) has been shown to be incapable of providing correct filter action. Accordingly, it is preferred to utilize a distribution of fibers of different diameters so that if the 0.10 to 1.23 μm range is divided into 2-5 equal divisions, especially 3 or 4 equal divisions, approximately equal numbers of fibers (preferably varying by no more than 10 number percent) will fall into each division (e.g. a 40, 30, 30; 30, 40, 30; or 35, 30, 35 number ratio upon division into three ranges of diameter).

Suitable filter sheets can be prepared by applying a mixture of glass fibers in a wet pulp in a paper-making machine. In some cases, a small amount of a high-polymer organic binder can be utilized although such binders are not preferred. Typical binders include cellulosic or acrylic polymers.

The glass fiber filters used in the practice of the invention are known as depth filters, being composed of irregularly filtering fibers. Separation is obtained mainly as a result of mechanical retention of particles. Because of both the irregular size and shape of the fibers, it is difficult to give an absolute pore size in such a filter. The filters are generally classified based on retention, which defines the capacity of a filter to remove particles of a given size from an aqueous or other solution.

In selecting glass filters, particle size retention, composition of glass thickness, and density should be taken into consideration in order to provide adequate filtration without hemolysis. A thickness of from 0.5 to 0.9 mm is preferred, with 0.50 to 0.80 being more preferred, particularly from 0.66 to 0.76 mm. Borosilicate and other glass that is slightly alkaline (pH 8.0–11.0, preferably about 9.0–10.5) is preferred. Particle size retention is preferably from about 1.0 to 3.0 microns, more preferably from 1.4 to 3.0 microns, and most preferably from 2.3 to 3.0 microns. A density in the range of from 0.10 to 0.30 g/cm$^3$ is preferred, more preferably 0.20 g/cm$^3$ to 0.28 g/cm$^3$, and most preferably about 0.25 g/cm$^3$. Since the approximate density of borosilicate glass is 2.61 g/cm$^3$, density can be seen to be a measure of the porosity of the glass filter.

The numbers set forth above are given for borosilicate glass filters. Particle size retention and thicknesses would be the same for other types of glass, although the densities would vary proporationately with the density of the respective glass selected.

A number of commercially prepared glass filters can be utilized in the practice of the invention. For example, Micro Filtration Systems (MFS) manufactures three glass fiber filters that can be utilized, identified by the manufacturing numbers GA-200, GB-100R and GC-90. GB-100R and GC-90 are utilized as doubled filters in the practice of the present invention. GA-200 has a density of approximately 0.25 g/cm$^3$, a thickness of 0.70 mm, and a retention size of 2.3 microns when filtering liquids. A double thickness of GB-100R has a density of 0.25 g/cm$^3$, a thickness of 0.76 mm, and a particle size retention of 2.0 micron. A doubled layer of GC-90 has a density of 0.30 g/cm$^3$, a thickness of 0.66 mm, and a particle size retention of 1.7 micron.

Whatman, Inc., of Clifton, N.J., and Schleicher & Schuell, a West German firm with a distribution in Keene, NH, also manufacture a number of different glass microfiber filters. However, none of the Whatman or Schleicher & Schuell filters tested (Whatman GF/C, GF/B, GF/D, GF/F, 934-4H; S+S 3362) has proven to be useful for the purpose of this invention, because of a difference in distribution of sizes of the glass fibers used to manufacture their filters and the resulting effects on red blood cell retention. Other glass fiber filters have also been tested and have been demonstrated not to provide adequate separation: P300, from Nucleopore, Pleasanton, CA (with organic binder); HB-5341 and BG-08005, from Hollingsworth & Vose, East Walpole, MA; glass fiber filter 111, 121, 131, 141, 151, and 161, from Eaton-Dikeman, Carlisle, PA; and glass fiber filters 85°/90° F., from by Machery & Nagel, Duren, West Germany.

All of the manufactured glass fibers described above (except where noted) are prepared without organic binders. Organic binders tend to reduce pore sizes and otherwise interact with red blood cells as they pass through filters. Accordingly, binderless glass filters are preferred. However, it may be possible to utilize binders in glass filters by selecting densities and fibers sizes that result in equal particle size retention. Furthermore, the strict control described does not need to be maintained when utilizing an agglutinin, as described below.

A number of different filter types were tested for their ability to effect the separation of plasma from serum using a device whose only motive force is capillary action. Of all the filters tested, binderless glass fiber filters having the distribution of fiber diameters discussed above gave the best separation. The pressure differential caused by capillary action is apparently significantly lower than that which exists either as a result of the action of gravity on larger samples or as a result of contact of a glass filter of the type described in U.S. Pat. No. 4,477,575, discussed above, with an absorbant pad. Typically, the available pressure is on the order of 2.5 mmHg (34 mm H$_2$O) or less.

Binderless glass microfiber filters having a volume of approximately 7–10 μl yielded about 3–4 μl of plasma when 25 μl of blood was applied. When the filter was utilized in a device as shown in FIG. 1, which is described in detail below, plasma appeared at the top of the filter outlet about five seconds after application of whole blood to the filter. Plasma appeared in the well about twelve seconds after application. Although blood cells eventually came through the filter, indicating that the blood cells were not being blocked but were being retarded, sufficient plasma had appeared by this time in order to conduct an adequate analysis. Filters of this type have been shown to be useful in filtering blood with hematocrits ranging from 33 to 60%. The ratio of plasma obtained to filter volume can be increased by utilizing larger diameter filter while maintaining the same filter thickness.

It is also possible to separate plasma from red blood cells in a single drop of blood in a capillary flow device using antibodies to red blood cells or other agglutinins in combination with a filter. The filter can be either the glass fiber filters described above (including the filters that do not work in the absence of agglutinins), paper, or any other type of filter that can filter agglutinated red blood cells. Paper, non-woven fabrics, sheet-like filter material composed of powders or fibers (such as carbon or glass fibers), and membranes having suitable pore sizes can all be utilized with antibodies and other agglutinins. Cellulose fibers, cotton linters, nitrocellulose, wood pulp, α-cellulose, cellulose nitrate, and cellulose acetate are all suitable for manufacturing acceptable filters and/or membranes.

Agglutinins can be present in the filter (in soluble form) or can be added to the blood sample prior to filtering (for example, by having a whole blood sample pass through a capillary or other chamber containing soluble agglutinins prior to contacting the filter). Any chemical or biochemical agent capable of causing agglutination of red blood cell can be used, including but not limited to antibodies and lectins. Such agglutinins are well known in the field of chemical analysis. Antibodies are preferred agglutinins, particularly for use with undiluted whole blood. However, other soluble agglutinins are also satisfactory, both for direct and indirect agglutination of red blood cells. See, for example, Stites et al., Basic and Clinical Immunology, 4th ed., Lange Medical Publications, Los Altos, CA, (1982), pp 356–359.

The antibodies utilized will have binding affinity for a determinant present on the surface of red blood cells. If a specific monoclonal antibody that reacts with a blood antigen is used, such as an antibody that reacts with type-A antigen, it will be necessary to match the blood type to the filter being used. Antibodies reactive with any antigen present on the surface of a red blood cell can be utilized, including but not limited to major histocompatability antigens, cell surface proteins, cell surface carbohydrates, and cell surface glycoproteins.

It is preferred to utilize a source of mixed antibodies that will react with all red blood cells of the species being tested. For example, an antiserum against human red blood cells can be utilized or a mixture of monoclonal antibodies that react with all of the major blood types. Such antibodies are available commercially. For example, an IgG fraction of rabbit anti-human red blood cell antibodies can be obtained from Cooper Biomedical (Westchester, PA). The antibody can be adsorbed onto the surface of the solid used to prepare the filter. In the case of paper filters, antibody can be effectively adsorbed onto paper by merely contacting the paper with an aqueous solution containing the antibody and then removing the water by evaporation. If desired, an antiserum can be applied neat or it may be diluted. There is generally a minimum amount of antibody that must be applied to the filter in order for filtration to be effective. If less than the minimum amount is present, red blood cells pass too quickly through the filter. However, it is not possible to give a specific amount of an antiserum that must be applied to the filter since different antisera will differ in their ability to bind red blood cells. Accordingly, the optimum amount of antibody is determined empirically. Serial two-fold dilutions of neat antibody-containing solution or antiserum are applied to filters in an amount sufficient to saturate the filter. Efficiency of filtration, lysis of red blood cells, and amount of plasma that passes through the filter when a standard amount of whole blood is applied are measured. When the IgG fraction of rabbit anti-human red blood cell antibody from Cooper Biomedical was utilized, the solution was reconstituted to give 30 mg/ml of protein and 20 mM phosphate-buffered saline at a pH of 7.3. The minimum volume of this solution that appeared to be necessary for good filtration was 7.5 μl (filter diameter 0.18 inch utilizing S+S GB003 paper; the filter volume was approximately 10 μl). However, it was not necessary to apply the antibody as a neat solution. Dilutions of 1:10 were still effective in providing efficient filtration. Accordingly, it appears that the volume of solution (10 μl in a 1:10 dilution) necessary to saturate the filter is more important than providing a high titer of antibody. When using a filter paper disk 0.180 inch in diameter and a volume of approximately 10 μl, at least 5 μl, preferably at least 7.5 μl of solution appeared to be necessary to saturate the disk and uniformly distribute the antibody throughout the filter. Similar volume ratios (0.5:1 and 0.75:1) will be effective for other filter volumes. Uniform distribution of antibody prevents red blood cells from passing through the filter at one location while being trapped in others.

If antibody is added to the sample prior to contact with the filter, it is preferred to carry out the filtration in the presence of an agent capable of suppressing hemolysis. Typical suppressing agents include local anaesthetics, such as dibucaine and lidocaine; β-andrenergic blockers, such as propanolol; tricyclic antidepressants, such as chlorpromazine and anitriptreine; and 3-hydroxypyridines, such as 3-hydroxy-6-methylpyridine.

It may be possible to utilize a filter, with or without antibody, to control the rate of passage of plasma or blood (the latter when utilizing a bare paper filter or other material that does not separate red blood cells from plasma). Increasing the amount of antibody on a filter increases the time that it takes the plasma front to reach a given location along the capillary path. The filter and the capillary leaving the filter each act as a point of resistance to the flow of fluid through the device. In effect, each acts as a valve in a fluid stream. When passage of fluid through the filter meets with more resistance than flow through the capillary, the system acts as if a first valve is partially closed while a second valve in the fluid stream is open. However, it is possible to vary the capillary flow rate so that greater resistance is present in the capillary. Such a system acts as if the first valve is open while the second valve is partially closed. By varying filter thickness and density and by selecting an appropriate capillary diameter, considerable control over flow of fluid through the system can be achieved.

The filter as described above has been utilized in the test devices described in U.S. patent application Ser. Nos. 880,793 and 762,748, which are herein incorporated by reference. A brief description of these devices is included here to show how the filter is used in combination with the remainder of a device that utilizes (1) small volumes of blood and (2) capillary action to cause movement of plasma.

A test device utilized in many of the experimental investigations described below is set forth in FIG. 1. The device was prepared from three plastic pieces approximately the size and shape of microscope slides and double-sided tape. Top slide 10 had a hole 12 smaller in diameter than the filter to be utilized drilled completely through slide 10 and double-sided tape 14, which in the embodiment shown does not extend the full length of the top slide but may do so if desired. Middle slide 20 has a hole 22 drilled completely through slide 20 and double-sided tape 24, which is applied to the bottom surface of slide 20. Double-sided tape 24 has a section 26A (a capillary space), 26B (a reaction chamber), and 26C (a capillary chamber extending to a vent) cut out of the tape to provide capillary channels and chambers when the total device is assembled. Capillary space 26A leads from hole 22, which holds the filter, to reaction chamber 26B. Capillary chamber 26C provides a vent by extending from the reaction chamber to the edge of the tape. Bottom slide 30 is a plain slide that forms a bottom surface of the filter, capillary, and reagent spaces formed by middle slide 20 and tape 24.

The assembled device is shown in FIG. 1C in which dotted lines are utilized to show the internal chambers that have been formed. Blood is applied at entry port (hole) 12, contacts the filter held in chamber 22, and is separated into plasma while the red blood cells are retained on the filter. Plasma passes through capillary 26A to reaction chamber 26B while air is vented through capillary vent 26C.

FIG. 2 shows a device prepared by welding two or more plastic pieces together to form a unitary device having internal chambers. Numerous embodiments of this device are set forth in U.S. patent application Ser. Nos. 880,793 and 762,748, referenced above. Blood is applied to entry port 42, which is smaller in diameter than chamber 44 which contains filter 46. Plasma exits the bottom of the filter into collecting space 48 and is transported by capillary 50 to reaction chamber 52. Vent 54 is provided for exit of air from the device. Ridges 56 may be provided if desired to aid in the application of blood to the entry port. Additional capillaries, chambers, vents, and the like such as are described in the incorporated patent applications may be present in device 40 but are ommitted in FIG. 2 for clarity.

A whole blood sample, optionally formulated by addition of anticoagulants or other reagents useful in collection of blood or in undergoing a reaction with the analyte that will be measured, is introduced into the entry port in the receiving unit of a test device. The receiving unit may be a capillary or a larger chamber. The receiving unit may be used to measure the particular sample volume or may simply serve to receive the sample and direct the sample to the filter. When whole blood contacts the filter, it is separated into its components as described above. The first component to leave the filter will be plasma or serum, depending on the source of the sample. For the remainder of this discussion the term plasma will be used but should be understood to represent either plasma or serum.

The filters of the present invention typically comprise a single layer of material rather than multiple layers. They are intended for separation of a single drop of blood, which typically has a volume of 30–50 $\mu$l or less. Accordingly, the volume of the filter is also small, typically in the range of 5 to 20 $\mu$l, in order to avoid absorbing and retaining all of the plasma. Thickness (i.e., measured in the direction of the flow path) is preferably in the range of 0.2–1.5 mm. This range is for all filters and thus is somewhat broader than that expressed for glass microfiber filters set forth above. Particle size retention for glass microfiber filters is discussed above. Filters used with agglutinins can be more porous if desired but should retain agglutinated red blood cells, which typically form clumps of cells with apparent diameters from 6–10 $\mu$m for a few cells to greater than 0.1 mm (100 $\mu$m) for a large number of cells.

The plasma will usually be picked up as it leaves the filter by one or more capillaries. When blood is applied to the top of a filter, plasma will be collected from the bottom. The sides of the filter are in close contact with the walls to prevent red blood cells from passing around the edges of the filter. Optionally, a sealer (usually a polymeric compound) can be used on the sides of the filter. Plasma leaving the bottom of the filter can collect in grooves or other spaces between the filter and the surface of the device containing the filter in closest contact with the bottom of the filter. Capillaries will draw plasma off from the collection space or spaces. It will be recognized that the words top, bottom, and sides as used here are relative terms and do not necessarily describe orientation of the filter in relation to the earth's surface. Capillaries will usually have diameters in the range of about 0.01 mm to 2 mm. The capillaries will vary in length but are generally shorter than 10 cm, usually not exceeding about 5 cm.

The first capillary may control the rate of flow into the chamber that will usually serve as the reaction chamber. Thus, the capillary may aid in the control of the time with which the plasma is in contact with a reagent contained within or bound to the walls of the capillary and/or reaction chamber. However, the flow rate of plasma through the filter is limiting in many instances, as described above, so that the capillary often is transporting plasma as fast as it leaves the filter. The reagent provides a color change or some other means of determining the amount of analyte present in the plasma.

The capillary provides the sole driving force for the movement of liquid through the device after passage of the sample through the filter. The device is normally employed with the capillaries, reaction chambers, and other chambers being oriented in a horizontal plane so that gravity does not affect the flow rate. The device is employed without ancillary motive force, such as a pump, gravity, or the like. Accordingly, it is essential to select a filter as described herein in order to achieve the separation while allowing capillary force to transport plasma through the device. Experimental evidence has demonstrated that the filters described in prior art such as U.S. Pat. Nos. 4,477,575 and 4,256,693, for separating large volumes of blood aided by gravity or which depend on relatively large wicking forces caused by absorbant substances that contact the filter, are ineffective in capillary flow devices of the type utilized in the present invention.

Although the filters described herein can be utilized in the same devices previously described, a preferred configuration for use of devices with glass fiber filters is shown in FIG. 3. In this device, whole blood is supplied to an entry port 42' situated above a filter, designated as a blood separater. A number of capillaries (50') are arranged at the periphery of the blood separater to transport plasma to the reagent area. The capillaries may be of different lengths and diameters but are designed to allow plasma to reach the reagent area 52' substantially simultaneously from each capillary. U.S. application Ser. No. 880,793 describes sizing capillaries to achieve this affect. This design allows for uniform and rapid filling of the reagent area.

The invention will now be further described by reference to certain specific examples which are included for purposes of illustration only and are not to be considered limiting of the invention unless otherwise specified.

EXAMPLE I

Materials and Methods

Blood

Whole blood in 15 USP units/ml of lithium heparin was used in the following experiments.

Filter disks

The filter disks were made from commercially available filters or other indicated materials by using a 0.180" punch.

Welded Cartridges

ABS (acrylamide butadiene styrene) slides were welded with the Branson ultrasonic welder at the following settings: pressure=60 psi, weld time=0.3 sec, hold time=1.5 sec, down speed=3.0.

The essential parts of the device were a filter chamber 33.5 mil thick with a total volume of 16 $\mu$l, a connecting chamber (wider than a normal capillary) 3.5 mm thick, and a reaction chamber with vent hole. The total volume of the connecting chamber and reaction chamber was 8.5 $\mu$l.

Tape Slides

Acetate plastic strips (6"×1") were washed in Sparkleen solution, rinsed in deionized water, and then dried using lint free towels. The plastic strips were then cut into 2.5"×1" slides. Plastic surfaces that contacted plasma were etched in a plasma etcher prior to assembly. The top slide was a clean piece of plastic with a 1"×0.5" double stick tape piece stuck to the bottom of the slide. A doublesided, 3.5 mil thick, Scotch brand tape with a pattern that formed capillaries and other internal chambers cut out of the tape was stuck to the bottom of what would be the middle slide. A hole was drilled to form the well using a #16 drill (0.173"). A #25 drill was used to make a vent hole in this cover slide. The top strip was stuck to the top of the middle strip with the holes carefully aligned. The filter of choice is then placed in the well of the middle slide, and a bottom etched slide was stuck to the middle slide's tape. The filter was flush against the top surface of the bottom slide. The finished slide is shown in FIG. 1.

Hemolysis Measurement

The percentage hemolysis was quantitated by measuring the absorbance of 570 nm light by the plasma. Absorbance was measured on a Hewlett-Packard 8451A spectrophotometer. The readings were taken using cells having path lengths of approximately 0.01 cm. The 0.01 cm path length was in a tape cartridge prepared as described above. The absorbance was converted to percent hemolysis by multiplication of the absorbance by a conversion factor. The peak at 570 nm was used for the 0.01 cm pathlength cell, and the conversion constant was 42.0.

Glass Fiber Filters

A number of glass fiber filters were tested, including GA-200 from Micro Filtration Systems (MFS), which is the filter used in all examples unless another filter is specified. GA-200 is a non-woven glass fiber filter containing glass microfibers having typical diameters in the range from 0.5 to 1.0 micrometer. The filter is 0.70 mm thick and retained particles 2.3 $\mu$m in diameter in the liquid phase. The density of the filter is 0.25 g/cm$^3$. Density and thickness values are given prior to the slight compression that took place during the process of fabricating the capillary device.

Results

Blood from a patient with sickle cell anemia, blood with artificially produced high and low hematocrits, and normal blood were filtered through the GA-200 filters to determine if blood with an abnormal hematocrit would be effectively filtered.

| Blood Type | Filtration | Time 1* (sec) | Lysis (%) |
|---|---|---|---|
| sickle cell | + | <5 | 0.80 |
| HCT = 30 | + | <5 | — |

| Blood Type | Filtration | Time 1* (sec) | Time 2* (sec) | Volume** ($\mu$l) |
|---|---|---|---|---|
| Fresh blood | | | | |
| HCT = 48.5 | + | 4 | 12.6 | 2.5 |
| | + | 5 | 13 | 2.5 |
| HCT = 33.0 | + | 4 | 8.9 | 5 |
| | + | 5 | 12.7 | 5 |
| HCT = 60.0 | + | 4 | 13.2 | 2.5 |
| | + | 8 | 27 | 2.5 |
| | + | 7 | 12 | 2.5 |

*Time 1 is the time between the addition of the blood to the filter and the exiting of red blood cells from the filter. Time 2 is the time for the blood to reach the beginning of the reagent well.
**Volume = the volume of plasma which exited the filter before red blood cells exited the filter.

It is evident that the filters are as effective in filtering the abnormal hematocrit blood as they are with normal blood; in fact, lower hematocrit blood appears to flow through the filters faster than normal or high hematocrit blood.

The lower hematocrit blood was more efficiently filtered; that is, more volume plasma per volume of blood exited the filters before the red blood cells. However, sufficient plasma was separated even in high hematocrit blood to allow plasma testing.

Comparison of Filters from MFS

A variety of filters from Micro Filtration Systems were tested for the ability to filter RBCs from plasma. The nomenclature of the MFS filters is based on their physical properties. The further along the second letter of the name is in the alphabet, the tighter the weave of the filter and the slower the flow through the filter. The numbers in the name correspond to the thickness of the filter; that is, the higher the number, the thicker the filter. Three filters from the group examined proved satisfactory: the GA-200, two GB-100R stacked on top of each other, and two GC-90 stacked on top of each other.

| Filter | Time 1 (sec) | Time 2 (sec) | Volume (μl) | % Lysis* |
|---|---|---|---|---|
| GA-200 | 5.0 | 12.8 | 4 | 0.58 |
| GB-100 × 2 | 19 | 32 | 5 | 0.95 |
| GC-90 × 2 | — | 120 | 5 | — |

*Lysis measured after removal of red blood cells by centrifugation = 0.37%

Analyte Recovery After Exposure to Glass Fiber Filter

The purpose of this experiment was to determine if potential analytes would be adsorbed by the glass fiber filter material. The analytes tested were cholesterol, potassium, and total protein. The experiment was conducted using the following protocol.

1. Serum was obtained from whole blood by drawing the blood into glass Vacu-tainer tubes, transferring the blood to centrifugation tubes, letting the blood stand at room temperature for 20 minutes and then centrifuging for 5 minutes at the blood setting on a TRIAC centrifuge (Clay Adams).
2. The sample was then split, one sample being contacted with the glass fiber filter material and the other being left alone until laboratory analysis.
3. The volume of the filter disks in the tape slides was 12.6 μl. Assuming 50 μl of blood is added to the filter, the ratio of blood volume to filter volume was approximately four. In the experiment, 2 ml of serum was contacted with a 24 mm diameter disk (depth=0.7 mm) with a total volume of 317 μl. The blood/filter volume ratio was 2000/317=6.3 in the experiment.
4. The samples containing filters were vortexed at medium speed for about 20 seconds and then spun in a TRIAC centrifuge for 5 minutes to spin down the glass fibers. The serum was drawn off using a glass pipet. The serum was then analyzed.

| | Without filter | With filter | Fraction recovered |
|---|---|---|---|
| CHOLESTEROL (mg/dl) | 157 | 158 | 1.01 |
| POTASSIUM (mEq/ml) | 4.2 | 4.2 | 1.00 |
| TOTAL PROTEIN (gm/dl) | 7.2 | 7.1 | 0.99 |

The potassium, total protein, and cholesterol results indicate that there was almost complete recovery of these analytes after contact with the filter.

All publications and patent applications cited in the specification are indicative of the level of skill of those skilled in the art to which this invention pertains. Each publication is individually herein incorporated by reference to the same extent as if each individual publication and patent application had been incorporated by reference individually in the location where cited.

Although the foregoing invention has been described in some detail by way of illustration and example for purposes of clarity and understanding, it will be obvious to those skilled in the art that certain changes and modifications may be practiced within the scope of the appended claims.

What is claimed is:

1. In a clinical diagnostic device comprising a housing having a fluid inlet port, a vented reaction area, and a unitary capillary pathway connecting said inlet port and said reaction area, said housing constructed such that said pathway conducts liquid exclusively as a result of capillary pressure originating in said pathway, the improvement which comprises:

a low-pressure filter in said inlet port and directly adjacent to said capillary pathway, wherein said filter is constructed so as to separate agglutinated red blood cells from plasma, wherein said filter further contains a soluble agglutinin for agglutinating red blood cells selected from the group consisting of antibodies and lectins, wherein whole blood applied to said inlet port contacts said soluble agglutinin concurrently with contacting said filter and plasma is separated from whole blood which flows into said capillary pathway in the absence of externally applied pressure.

2. The device of claim 1, wherein said agglutinin is an antibody.

3. The device of claim 1, wherein said agglutinin is a lectin.

4. The device of claim 1, wherein said filter is constructed of a material selected from the group consisting of glass fibers, paper, and porous membranes.

5. The device of claim 1, wherein said filter comprises paper and is constructed so as to retain particles having a diameter of 6 μm.

6. The device of claim 1, wherein said filter is constructed so as to retain particles having a diameter of 6 μm.

7. The device of claim 1, wherein said filter is constructed so as to retain particles having a diameter of 1 μm.

* * * * *